United States Patent [19]

Park

[11] Patent Number: 5,327,778

[45] Date of Patent: Jul. 12, 1994

[54] APPARATUS AND METHOD FOR VISCOSITY MEASUREMENTS USING A CONTROLLED NEEDLE VISCOMETER

[76] Inventor: Noh A. Park, 914 Fillmore Rd., Norristown, Pa. 19403

[21] Appl. No.: 833,017

[22] Filed: Feb. 10, 1992

[51] Int. Cl.$^5$ ............................................. G01N 11/12
[52] U.S. Cl. .................................... 73/54.21; 73/54.15
[58] Field of Search ................. 73/54.15, 54.16, 54.21

[56] References Cited

U.S. PATENT DOCUMENTS

| | | |
|---|---|---|
| 358,877 | 3/1887 | Perkins . |
| 989,822 | 4/1911 | Strasburger . |
| 1,748,512 | 2/1930 | Knopf . |
| 1,894,369 | 1/1933 | Duffing . |
| 2,491,389 | 12/1949 | Norcross ............................ 73/54.18 |
| 4,637,250 | 1/1987 | Irvine et al. . |
| 4,852,388 | 8/1989 | Park et al. . |

FOREIGN PATENT DOCUMENTS

| | | |
|---|---|---|
| 611575 | 12/1960 | Canada . |
| 950506 | 10/1956 | Fed. Rep. of Germany . |
| 620898 | 7/1978 | U.S.S.R. . |
| 751958 | 7/1956 | United Kingdom . |
| 931471 | 7/1963 | United Kingdom . |

OTHER PUBLICATIONS

G. S. Smith, The Plunger Rheometer-Law of Flow For a Newtonian Liquid, Aug., 1957, pp. 227-230 of Min. of Supply, Aeronautical Inspection Directorate.
J. Lohrenz, G. Swift and F. Kurata, An Experimentally Verified Theoretical Study of the Falling Cylinder Viscometer, Dec. 1960, pp. 547-550 of A.I. Ch.E. Journal.

Primary Examiner—Hezron E. Williams
Assistant Examiner—Nashmiya Ashraf
Attorney, Agent, or Firm—Reed Smith Shaw & McClay

[57] ABSTRACT

An apparatus and method are disclosed for accurately determining viscosity of Newtonian and non-Newtonian fluids using a controlled needle viscometer. The controlled needle viscometer includes a vertical sample insert tube filled with the liquid of which the viscosity is to be determined. Using a needle guide at the top of the sample insert tube, a body having a known density is made to fall through the liquid in the sample insert tube. Using the time that the controlled needle takes to fall between two known distance marks or transducers, the velocity of the needle falling through the liquid is determined. Thus, the viscosity can be calculated by using the velocity of a controlled needle. In the method, viscosity, shear rate and shear stress can be calculated according to a modified power law model.

10 Claims, 5 Drawing Sheets

APPARATUS AND METHOD FOR VISCOSITY MEASUREMENTS USING A CONTROLLED NEEDLE VISCOMETER

BACKGROUND OF THE INVENTION

This invention relates to an apparatus and method for accurately determining the viscosity of Newtonian and non-Newtonian fluids by means of a controlled needle viscometer. The controlled needle viscometer includes a vertical sample insert tube filled with the liquid of which the viscosity is to be determined. Viscosity of the sample can be determined by measuring the time of fall of a controlled needle through a predetermined distance of the fluid held in a sample insert tube.

A fluid can generally be classified as ideal, Newtonian or non-Newtonian based on its behavior under stress. An ideal fluid has no shear stress in a flow field and its viscosity is zero. No fluids which exhibit this type of behavior in fact exist. In a Newtonian fluid, such as water and glycerol, the shear stress is directly proportional to the shear rate, and its viscosity is independent of the shear rate. In a non-Newtonian fluid, the shear stress is dependent on the shear rate, and its viscosity may vary with the shear rate in a complex manner.

Viscosity is a function of internal friction and of the behavior of a fluid under stress. Therefore, in order to improve the design of pumps, stirrers, mixers, liquid transport devices, and reactors, it is important to be able to accurately determine viscosity. Furthermore, because the molecular weight of a polymer solution is related to its viscosity at zero shear rate, an accurate determination of the zero shear rate viscosity of a polymer solution enables one to obtain an accurate measurement of its molecular weight.

Many methods have been developed to determine the viscosity of fluids. The earliest is the capillary type viscometer, in which a fluid flow is provided through a capillary tube and the drop in pressure across a length of the tube is used to determine the viscosity. This technique suffers from many disadvantages, such as the need for measuring small pressure differences accurately, calibrating the diameter of the capillary tube and keeping the capillary tube clean. Furthermore, it has been found that the capillary tube viscometer is only useful for determining viscosity at high shear rates. It cannot be used to determine viscosity at low shear rates.

Another known technique is falling sphere or falling ball viscometry, first described in G. G. Stokes, Camb. Phil. Trans., 9, p. 8 (1851). In this method the viscosity is determined from the time taken for a sphere to fall through a predetermined distance in an infinite fluid. However, in the falling sphere method, the following assumptions are made: (a) the spheres are falling in an infinite medium, and (b) the density of the falling sphere is in a suitable range for the equation used to determine the viscosity to hold true. Furthermore, the falling sphere must be perfectly round, so that it will fall vertically through the fluid and will not veer in one direction or another or fall erratically.

In practice, spheres can only be made from a limited range of materials, such as, glass, aluminum or steel and their density cannot be adjusted. Further, very few spheres are truly round and, as a consequence, the fall through the fluid medium is often not vertical. Moreover, a fluid must be held in a container. Therefore, the fluid is not, in fact, infinite, and wall effects have to be considered. Thus, inaccuracies arise from the non-vertical fall of a sphere and a correction factor for wall effects must be applied. The falling sphere method does not provide an exact analytical solution for non-Newtonian fluids because of the geometric complexities involved.

Falling cylinder and plunger viscometers have also been designed. See, Lohrentz, et al., A. I. Ch. E. Journal, 6, No. 4, p. 547-549 (1960) and G. S. Smith, J. Inst. Pet., 43, p. 227-230 (1957). Some deficiencies of these viscometers are difficulties in constructing the falling cylinder or plunger; difficulties in obtaining cylinders or plungers with different densities; and difficulties in maintaining a vertical fall through the fluid. To maintain a vertical fall through the fluid, guide pins or bushings are required. Further, the eccentricity effect is very significant. Because of these problems, it is difficult to account for the systematic error in viscosity measurement by the falling cylinder or plunger method.

A rotating cylinder viscometer with two coaxial cylinders, a rotating outside cylinder with a stationary inside cylinder, has been developed to measure the viscosity of non-Newtonian fluids. See Van Wazer et al., Viscosity and Flow Measurement, p. 47-96, Interscience Publishers, New York, 1963. However, the rotating cylinder viscometer is difficult and expensive to make because small torque measurements on the stationary spindle are needed for compensation purposes. Further, it is very difficult to maintain a constant temperature in the system and evaporation of the fluid from the open mouth container is unavoidable. These difficulties are often translated into unacceptably large errors in the viscosity measurement obtained.

Recently, a relatively simple and easily used apparatus and method for the accurate determination of the viscosity of Newtonian and non-Newtonian fluids was developed. That apparatus is the subject of U.S. Pat. No. 4,637,250, issued Jan. 20, 1987, entitled Apparatus and Method For Viscosity Measurements For Newtonian and Non-Newtonian Fluids, to Irvine and Park (the present inventor). The disclosure of that patent is incorporated herein by reference as if set forth in full. The patented apparatus includes a cylinder for holding the fluid for which the viscosity is to be determined; a needle; a needle launcher placed at the top of the cylinder for feeding the needle into the fluid in the cylinder; means at the bottom of the cylinder for collecting the needle; means for maintaining the cylinder, the sample insert tube, and its contents at a constant temperature; and means for measuring the time of fall of the needle between two marks on the wall of the cylinder spaced a predetermined distance. The needle is capable of being adjusted in density, and viscosity is measured by allowing the needle to fall through the liquid in the sample insert tube while maintaining the sample insert tube and its contents at a constant temperature. The time of fall of the needle between the spaced marks on the cylinder (or between transducers) is measured. From this measurement and the dimensions of the apparatus, the viscosity can be calculated.

It is an object of this invention to provide an inexpensive and easily used apparatus and method to determine accurately the viscosity of Newtonian and non-Newtonian fluids over a wide range of viscosities.

BRIEF SUMMARY OF THE INVENTION

In accordance with the present invention, a testing body, sometimes referred to as a "controlled needle", is pushed down through a fluid sample using external weights. The controlled needle is preferably composed of a cylindrical needle with hemispherical tips.

An upwardly extending weight support bar is connected to the needle. The "effective" density of the needle is controlled by adding or removing weights from the weight support bar. Thus, because the weights may vary selectively over a wide range, even extremely viscous materials like tooth paste, gel, dough materials, can be measured easily. Not only can this apparatus measure the viscosity of extremely viscous materials, greater than $10^8$ cPs., but it can also measure viscosity at high shear rates. Also, the viscosity of a dilute solution can be measured at both low and extremely high shear rates, more than one million reciprocal seconds. With a light sensing system or laser, even the viscosity of paramagnetic slurry can be measured. The viscous properties of melted plastics, metals and other materials at very high temperature, higher than 1500° C., can also be measured with the present invention. The controlled needle technique can be applied to portable and disposable viscometers, and can be used in various industries such as food, paint, pharmaceutical, chemical, oil, petroleum etc. to measure viscosity accurately and simply. The present invention can also be used to measure the viscosity of very small samples, less than 0.5 ml of precious and expensive materials, for example.

The apparatus is simple and easy to use, and equations have been derived for the accurate determination of the viscosity of Newtonian and non-Newtonian fluids from the data collected by using the apparatus.

In general, in a presently preferred form, the apparatus is as follows:

A sample insert tube, of inside diameter "D" cm, is provided, for holding a sample of the fluid of which the viscosity is to be determined. The wall of the tube has a predetermined distance, "F", marked along its vertical axis, the top mark F being at least "D" from (below) the level of sample, and the bottom mark being at least "D" from the bottom of the sample insert tube. A controlled needle, preferably made of a bored rod or tube of material selected from the group comprising Teflon, glass, aluminum, stainless steel and ceramic, is connected to a bar or rod, to in effect vary the density of the controlled needle. Weights associated with the needle, which may be externally supported by the rod may selectively be varied over a wide range, to produce a velocity of fall of the needle from almost 0 to about 50 cm per second. The preferred needle is hemispherically sealed at both ends, and has a diameter $d_2$ cm, wherein $k_2 = d_2/D$ is preferably at least about 0.2 and at most about 0.95, and has a length of N cm, wherein N/D is at least 2.0.

In the presently preferred form of the invention, a rod coupled to the needle provides a convenient way to apply weights to the needle.

A needle guide is disposed atop the sample insert tube and a cap placed above the needle guide. The guide provides a pair of vertically aligned bores coaxial with the vertical axis of the sample insert tube. The rod is received in the bores and aids in aligning the needle with that axis.

Means are provided for maintaining a constant temperature in the sample insert tube, and others are provided for measuring the time of the fall of the controlled needle the predetermined distance.

In one presently preferred form of the invention, the sample insert tube has a double wall i.e. a water jacket, with an inlet and outlet to permit the circulating of water or oil at a constant temperature. Thermocouples or RTDs may be inserted into the space between the walls to monitor the temperature in the apparatus. The time of fall may be measured by eye, with a stopwatch, or by electronic, magnetic or light means.

In general, in its method aspect, the invention involves the steps of:

a. filling the sample insert tube with a fluid for which the viscosity is to be determined;
b. placing the needle guide atop the sample insert tube, with the guide rod for the needle received in the bores;
c. inserting the needle into the fluid;
d. activating the means for maintaining a constant temperature in the sample insert tube and the fluid;
e. allowing the temperature of the controlled needle to reach the temperature of the fluid;
f. allowing the controlled needle to fall through the fluid sample in the sample insert tube;
g. measuring the time in "t" seconds taken for the controlled needle to fall the predetermined distance marked on the wall of the cylinder; and
h. for Newtonian fluids, calculating the viscosity by using the equations described in detail below.

For determining the viscosities of non-Newtonian fluids, the above procedure is modified as follows:

The time of fall is measured for at least three different densities by securing to the guide rod of the controlled needles in successive test runs three different weights. The viscosity is then calculated according to a modified power law model, also described in detail below:

For the purpose of illustrating the invention, there is shown in the drawings a form of the invention which is presently preferred. It should be understood, however, that the invention is not limited to the precise arrangements and instrumentalities shown.

BRIEF DESCRIPTION OF THE DRAWINGS

There are seen in the drawings forms of the invention which are presently preferred (and which represent the best mode contemplated for carrying the invention into effect) but it should be understood that the invention is not limited to the precise arrangements and instrumentalities shown.

DETAILED DESCRIPTION OF PREFERRED EMBODIMENT

Figure 1:
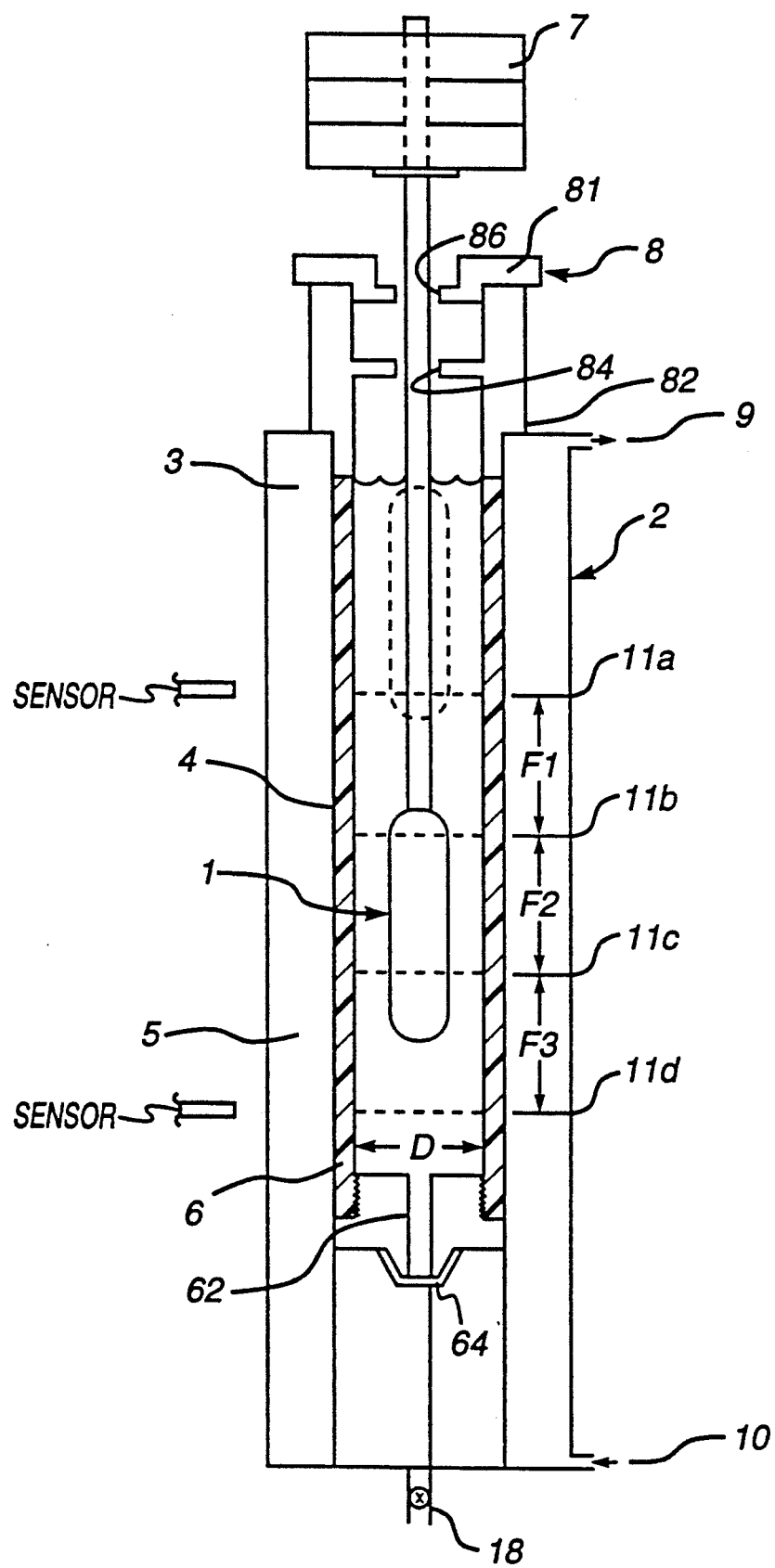
FIG. 1 is a schematic presentation, in side elevation and cut away, of controlled needle viscometer in accordance with the present invention.

Referring now to the drawings in detail, wherein like elements are designated by like reference numerals, there is seen in FIG. 1 a controlled needle viscometer designated generally by the reference numeral 2. The viscometer 2 includes a cylinder 4 and a sample insert tube 6 of inside diameter "D" cm, and preferably made of a transparent material, such as plastic (e.g. epoxy resin), quartz, or borosilicate glass. The sample insert tube 6 may also be made of opaque material, such as Teflon, stainless steel, aluminum, or ceramic. The sample insert tube 6 is depicted as containing the sample liquid, i.e. the liquid whose viscosity is to be determined. A jacket 3 of transparent or opaque material surrounds the cylinder 4 and sample insert tube 6 and forms with the cylinder 4 a generally cylindrical chamber 5. The jacket 3 has an inlet 10 at one end and an outlet 9 at other end for the flow of a heated or cooled liquid through the chamber 5 to maintain the sample insert tube 6 and its liquid contents at a constant temperature. On the wall of the cylinder 4 is a series of marks 11a, 11b, 11c and 11d or sensors which are spaced apart at predetermined distances F1, F2 and F3 along a portion of the length of the cylinder 4.

A controlled needle, designated generally by the reference numeral 1, is depicted within the sample insert tube 6. The velocity of the controlled needle may be determined as it passes the marks 11a, 11b, 11c and 11d. For the purposes of illustration, the needle 1 is shown in FIG. 1 in two positions, one in phantom at approximately the point of insertion into the sample liquid and another as it passes mark 11b during its passage through the sample insert tube 6.

Figure 2:
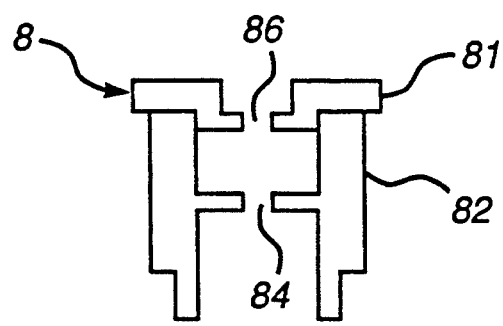
FIG. 2 is a schematic view, in side elevation and cut away, of a needle guide used in the apparatus shown in FIG. 1.
Figure 3:
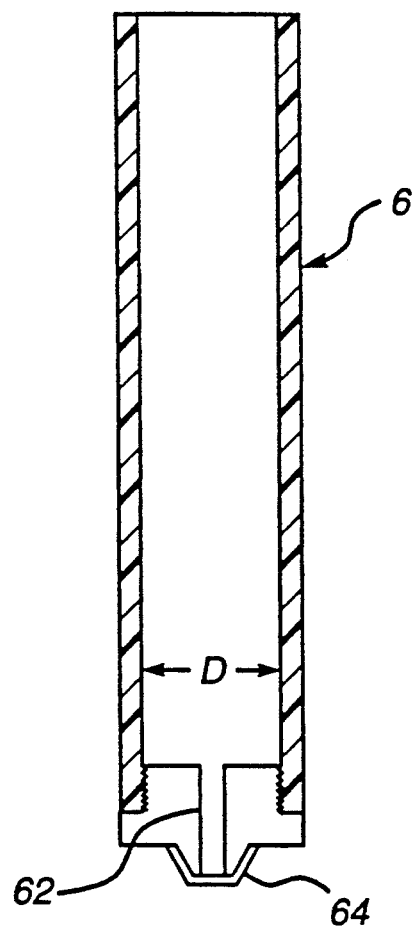
FIG. 3 is a schematic view, also in side elevation and cut away, of a disposable sample insert tube used in the apparatus shown in FIG. 1.

Referring again to FIG. 1, and also to FIG. 2, a needle guide, designated generally by the reference numeral 8 is affixed to the top of the sample insert tube 6. As is perhaps best seen in FIG. 2, the needle guide 8 has a cylindrical outer wall 82 which adjoins the cylinder 4. The needle guide also has a central bore 84 which is coaxial with the vertical axis of the cylinder 4. Associated with the needle guide 8 is a cap 81, which also has a central bore 86, aligned with the bore 84 in the needle guide 8.

The sample insert tube 6 has a bottom nipple 62 to facilitate connection of a syringe, for applying suction to load or remove a fluid sample. A bottom cap 64 is provided to close the nipple 62.

Figure 4:
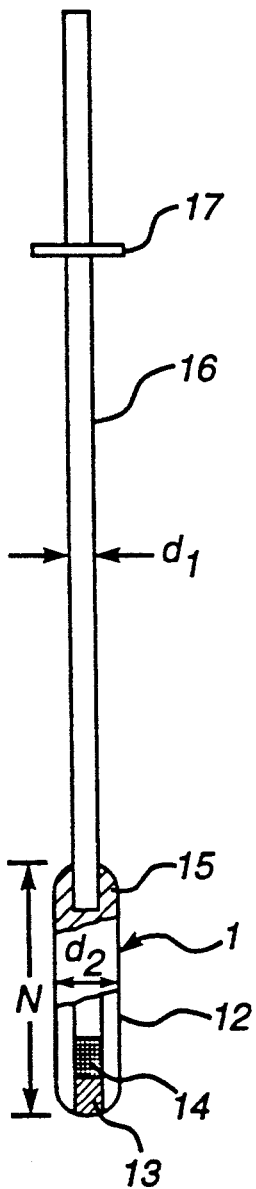
FIG. 4 is a sectional view, in side elevation and partly broken away, of a controlled needle used in the apparatus shown in FIG. 1.
Figure 5:
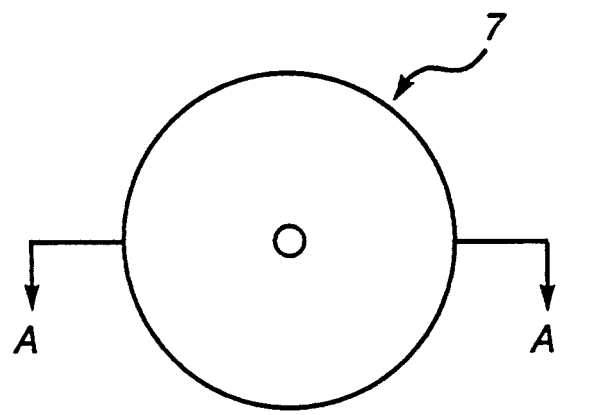
FIG. 5 is a top plan view of a weight used in the apparatus shown in FIG. 1.
Figure 6:
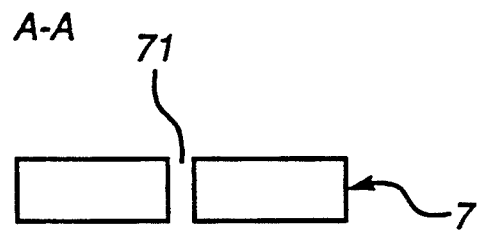
FIG. 6 is a side elevation view of the weight depicted in FIG. 5.

Referring now to FIG. 4, the control needle 1 will be described in detail. As is shown in FIG. 4, the needle 1 used in the viscometer 2 comprises a tube 12, preferably made of a material such as Teflon, glass, aluminum, stainless steel or ceramic, and having an outer diameter, $d_2$, which is preferably more than 0.2 but no greater than 0.95 times the inside diameter, D, of the sample insert tube 6 and a length, N, which is at least 2.0 times the inside diameter, D, of the sample insert tube 6. The tube 12 of the needle 1 is provided with hemispherical tips 15 and a weight support bar, or rod, 16 which serves to support weights 7 and guide the needle 1. The support bar 16 is threaded, glued or otherwise suitably affixed to the upper tip 15 of needle tube 12. A collar 17 associated with the weight support bar 16 provides a support for weights 7, the purpose of which is explained below.

Referring again to FIG. 4, weight enhancing ballast elements 14, such as metal wires or shot can be placed in the tube 12 of the needle 1 to adjust the density of the needle 1. Also, weights 7 can be applied to the weight support bar 16 to adjust the density of the needle 1. A bar magnet 13 can be associated with the tube 12, as shown in FIG. 4, to trigger the timer of a magnetic sensing time measurement system (seen schematically in FIG. 1). After the desired density for the needle 1 is obtained by inserting an appropriate quantity of ballast 14 and a magnet 13, the ends of the tube 12 may be sealed as by tips 15. The weights 7 may be made of Teflon, aluminum, stainless steel or ceramic to adjust, and are provided with central openings 71, complemental with the diameter of the bar 16. The number of weights 7 can be varied selectively for different needles of different desired effective densities.

To determine the viscosity of a liquid, the sample insert tube 6 is filled with the liquid and the needle guide 8 is seated on top of the sample insert tube 6. A flow of a circulating liquid at a desired temperature is provided through the jacket chamber 5 to bring and maintain the cylinder 4, the sample insert tube 6 and its contents at a constant temperature. A weight support bar 16 is inserted through the aligned bores 84 and 86 of the needle guide 8 and cap 81. The collar 17 is attached to the weight support bar 16 to hold the weights 7. The weights 7 are added to the weight support bar 16 to adjust the effective density of the controlled needle 1. It will be understood that as the controlled needle 1 falls through sample insert tube 6, the time, "t", in seconds, for the controlled needle to fall between two of the marks or sensors (as depicted by reference numerals 11a, 11b, 11c and 11d in FIG. 1) is measured.

For Newtonian fluids, the method of determining viscosity using the above apparatus is as follows:

a. First, the sample insert tube 6 is filled with a fluid whose viscosity is to be determined;

b. Next, the needle guide 8 and an associated controlled needle are placed on the top of the sample insert tube 6 and the controlled needle 1 is inserted into fluid.

c. The means for maintaining a constant temperature in the sample insert tube 6 is activated, and the temperature of the controlled needle 1 is allowed to reach the temperature of the fluid;

d. The needle is then made to fall through the sample insert tube 6; and the time, t seconds, is measured for the controlled needle 1 to fall the predetermined distance F marked on the wall of the cylinder.

The viscosity can then be calculated, using the following equations:

$$\eta = \frac{(\rho_s - \rho_f)g}{UG} = \frac{(\rho_s - \rho_f)g}{(U_t/ECF)G}$$

where $$G = \frac{8(1 + k_2^2)}{k_2^2(1 - \ln k_2) - (1 + \ln k_2)} \cdot \frac{1}{d_2^2}$$

$$U = U_t/ECF = (F/t)(1/ECF)$$

$$ECF = \frac{1 + (2/3)(d_2/L_2) + (d_1/d_2)^2(L_1/L_2)}{1 + (3/(2Cw))(d_2/L_2)(1/B_2) + (L_1/L_2)(B_1/B_2)}$$

-continued $$B_1 = \frac{k_1^2 + 1}{(k_1^2 - 1) - (k_1^2 + 1)\ln k_1}$$

$$B_2 = \frac{k_2^2 + 1}{(k_2^2 - 1) - (k_2^2 + 1)\ln k_2}$$

Cw=0.9999456−2.08324k$_2$−0.2822582 k$_2^2$+3.392001 k$_2^3$−2.58148k$_2^4$+0.554073k$_2^5$

In the above equations:
k$_1$=d$_1$/D
k$_2$=d$_2$/D
Cw=the Wall correction factor of sphere
d$_1$=support bar 16 diameter
d$_2$=controlled needle 1 diameter or hemispherical tips 15 diameter
D=inside diameter of sample insert tube 6
ECF=End Correction Factor of the controlled needle 1
F=predetermined distance of fall
L$_1$=(immersed length of bar 16 before dropping controlled needle) plus (a half of predetermined distance of fall)
L$_2$=controlled needle length minus one diameter of controlled needle 1
ρ$_s$=density of controlled needle 1
ρ$_f$=density of fluid
g=the gravity constant
t=the time of fall
U$_t$=terminal velocity of controlled needle (F/t)

The method for determining the viscosities of non-Newtonian fluids involves a modification of the above procedure, as follows:

The time of fall is measured for at least three different densities by adding three different weights 7 to the controlled needle 1. The viscosity is then calculated according to the modified power law model as follows:

1. "U" is calculated as follows:

$$U = U_t/ECF = (F/t)(1/ECF)$$

where $$ECF = \left[\frac{1 + (2/3)(d_2/L_2) + (d_1/d_2)^2(L_1/L_2)}{1 + (3/2(Cw))(d_2/L_2)(1/B_2) + (L_1/L_2)(B_1/B_2)}\right]^{1/n}$$

-continued $$B_1 = \frac{k_1^2 + 1}{(k_1^2 - 1) - (k_1^2 + 1)\ln k_1}$$

$$B_2 = \frac{k_2^2 + 1}{(k_2^2 - 1) - (k_2^2 + 1)\ln k_2}$$

Cw=0.9999456−2.08324k$_2$−0.2822582k$_2^2$+3.392001⋅k$_2^3$−2.58148k$_2^4$+0.554073k$_2^5$
k$_1$=d$_1$/D
k$_2$=d$_2$/D
Cw=the wall correction factor of sphere
d$_1$=diameter of the bar 16
d$_2$=diameter of the controlled needle 1 or diameter of hemispherical tips 15
D=the inside diameter of sample insert tube 6
ECF=end Correction Factor of the controlled needle 1
F=predetermined distance of fall
L$_1$=(immersed length of bar 16 before dropping controlled needle) plus (a half of predetermined distance of fall) controlled needle L$_2$=length minus one diameter of controlled needle
ρ$_s$=density of controlled needle
ρ$_f$=density of fluid
g=gravity constant
t=the time of fall
U$_t$=terminal velocity of controlled needle (F/t)

2. The flow index, n, where;

$$n = \frac{d[\ln(\rho_s - \rho_f)]}{d[\ln U]}$$

is determined from the slope of ln $(\rho_s - \rho_f)$ vs. ln U

3. The shear rate is then calculated as follows:

$$\gamma = 2UA(k_2,n)/D$$

where A(k$_2$,n)=Dimensionless number (refer to Table 1)

4. The viscosity is then calculated as follows:

$$\eta = \frac{(\rho_s - \rho_f)gD^2B(k_2, n)}{4U}$$

where B(k$_2$,n)=a dimensionless number (refer to Table 2 below)

TABLE 1

| | | | | | | | Values of A(k$_2$,n) | | | | | | | |
|---|---|---|---|---|---|---|---|---|---|---|---|---|---|---|
| k  n | 0.1 | 0.2 | 0.3 | 0.4 | 0.5 | 0.6 | 0.7 | 0.8 | 0.9 | 1.0 | 1.1 | 1.2 | 1.3 | 1.4 | 1.5 |
| 0.01 | 870.88 | 391.86 | 229.82 | 150.24 | 103.91 | 74.776 | 55.725 | 42.896 | 34.015 | 27.698 | 23.086 | 19.636 | 16.996 | 14.936 | 13.287 |
| 0.02 | 455.63 | 202.40 | 118.81 | 78.122 | 54.913 | 40.558 | 31.206 | 24.857 | 20.391 | 17.150 | 14.730 | 12.880 | 11.433 | 10.280 | 9.3450 |
| 0.03 | 309.89 | 137.20 | 80.863 | 53.731 | 38.388 | 28.924 | 22.735 | 18.496 | 15.481 | 13.265 | 11.589 | 10.290 | 9.2628 | 8.4345 | 7.7559 |
| 0.04 | 236.68 | 104.73 | 62.043 | 41.643 | 30.163 | 23.082 | 18.430 | 15.223 | 12.922 | 11.215 | 9.9124 | 8.8947 | 8.0827 | 7.4231 | 6.8788 |
| 0.05 | 192.84 | 85.448 | 50.896 | 34.482 | 25.270 | 19.582 | 15.831 | 13.229 | 11.350 | 9.9465 | 8.8685 | 8.0206 | 7.3399 | 6.7839 | 6.3227 |
| 0.06 | 163.99 | 72.753 | 43.577 | 29.778 | 22.048 | 17.265 | 14.100 | 11.894 | 10.292 | 9.0888 | 8.1599 | 7.4255 | 6.8332 | 6.3472 | 5.9424 |
| 0.07 | 143.52 | 63.815 | 38.439 | 26.476 | 19.778 | 15.629 | 12.873 | 10.944 | 9.5372 | 8.4759 | 7.6527 | 6.9993 | 6.4702 | 6.0346 | 5.6706 |
| 0.08 | 128.33 | 57.222 | 34.659 | 24.048 | 18.108 | 14.422 | 11.966 | 10.241 | 8.9782 | 8.0217 | 7.2772 | 6.6841 | 6.2024 | 5.8045 | 5.4712 |
| 0.09 | 116.68 | 52.186 | 31.782 | 22.202 | 16.838 | 13.504 | 11.276 | 9.7068 | 8.5535 | 7.6773 | 6.9931 | 6.4465 | 6.0014 | 5.6328 | 5.3233 |
| 0.1 | 107.49 | 48.240 | 29.536 | 20.764 | 15.850 | 12.790 | 10.741 | 9.2925 | 8.2254 | 7.4123 | 6.7757 | 6.2658 | 5.8496 | 5.5042 | 5.2136 |
| 0.2 | 70.104 | 32.746 | 20.994 | 15.462 | 12.328 | 10.345 | 8.9929 | 8.0429 | 7.2899 | 6.7244 | 6.2747 | 5.9094 | 5.6072 | 5.3534 | 5.1375 |
| 0.3 | 63.732 | 30.986 | 20.582 | 15.623 | 12.776 | 10.951 | 9.9619 | 8.7757 | 8.0818 | 7.5394 | 7.1047 | 6.7491 | 6.4530 | 6.2030 | 5.9891 |
| 0.4 | 68.016 | 34.279 | 23.428 | 18.191 | 15.148 | 13.176 | 11.803 | 10.795 | 10.026 | 9.4214 | 8.9340 | 8.5333 | 8.1983 | 7.9142 | 7.6704 |
| 0.5 | 81.724 | 42.514 | 29.762 | 23.539 | 19.886 | 17.499 | 15.822 | 14.584 | 13.634 | 12.883 | 12.275 | 11.773 | 11.351 | 10.993 | 10.685 |
| 0.6 | 110.61 | 59.178 | 42.297 | 33.985 | 29.067 | 25.829 | 23.541 | 21.842 | 20.532 | 19.492 | 18.647 | 17.947 | 17.358 | 16.856 | 16.423 |
| 0.7 | 174.50 | 95.772 | 69.722 | 56.807 | 49.118 | 44.028 | 40.415 | 37.720 | 35.634 | 33.973 | 32.619 | 31.495 | 30.547 | 29.736 | 29.036 |
| 0.8 | 354.87 | 199.09 | 147.35 | 121.58 | 106.17 | 95.930 | 88.636 | 83.178 | 78.943 | 75.561 | 72.800 | 70.502 | 68.581 | 66.899 | 65.460 |
| 0.9 | 1298.9 | 743.63 | 558.78 | 466.43 | 411.04 | 374.15 | 347.84 | 328.10 | 312.77 | 300.50 | 290.47 | 282.11 | 275.05 | 268.99 | 263.74 |

TABLE 2

Values of $B(k_2,n)$

| k \ n | 0.1 | 0.2 | 0.3 | 0.4 | 0.5 | 0.6 | 0.7 | 0.8 |
|---|---|---|---|---|---|---|---|---|
| 0.01 | $5.7253 \times 10^{-6}$ | $1.2747 \times 10^{-5}$ | $2.1748 \times 10^{-5}$ | $3.3269 \times 10^{-5}$ | $4.8106 \times 10^{-5}$ | $6.6850 \times 10^{-5}$ | $8.9706 \times 10^{-5}$ | $1.1654 \times 10^{-4}$ |
| 0.02 | $2.1794 \times 10^{-5}$ | $4.9258 \times 10^{-5}$ | $8.4025 \times 10^{-5}$ | $1.2785 \times 10^{-4}$ | $1.8182 \times 10^{-4}$ | $2.4632 \times 10^{-4}$ | $3.2017 \times 10^{-4}$ | $4.0197 \times 10^{-4}$ |
| 0.03 | $4.7822 \times 10^{-5}$ | $1.0869 \times 10^{-4}$ | $1.8482 \times 10^{-4}$ | $2.7840 \times 10^{-4}$ | $3.8983 \times 10^{-4}$ | $5.1749 \times 10^{-4}$ | $6.5846 \times 10^{-4}$ | $8.0942 \times 10^{-4}$ |
| 0.04 | $8.3008 \times 10^{-5}$ | $1.8916 \times 10^{-4}$ | $3.2036 \times 10^{-4}$ | $4.7795 \times 10^{-4}$ | $6.6030 \times 10^{-4}$ | $8.6320 \times 10^{-4}$ | $1.0813 \times 10^{-3}$ | $1.3093 \times 10^{-3}$ |
| 0.05 | $1.2648 \times 10^{-4}$ | $2.8861 \times 10^{-4}$ | $4.8662 \times 10^{-4}$ | $7.1964 \times 10^{-4}$ | $9.8291 \times 10^{-4}$ | $1.2691 \times 10^{-3}$ | $1.5704 \times 10^{-3}$ | $1.8797 \times 10^{-3}$ |
| 0.06 | $1.7736 \times 10^{-4}$ | $4.0482 \times 10^{-4}$ | $6.7948 \times 10^{-4}$ | $9.9683 \times 10^{-4}$ | $1.3482 \times 10^{-3}$ | $1.7229 \times 10^{-3}$ | $2.1107 \times 10^{-3}$ | $2.5031 \times 10^{-3}$ |
| 0.07 | $2.3473 \times 10^{-4}$ | $5.3556 \times 10^{-4}$ | $8.9488 \times 10^{-4}$ | $1.3033 \times 10^{-3}$ | $1.7476 \times 10^{-3}$ | $2.2138 \times 10^{-3}$ | $2.6895 \times 10^{-3}$ | $3.1649 \times 10^{-3}$ |
| 0.08 | $2.9770 \times 10^{-4}$ | $6.7863 \times 10^{-4}$ | $1.1288 \times 10^{-3}$ | $1.6330 \times 10^{-3}$ | $2.1733 \times 10^{-3}$ | $2.7322 \times 10^{-3}$ | $3.2957 \times 10^{-3}$ | $3.8530 \times 10^{-3}$ |
| 0.09 | $3.6541 \times 10^{-4}$ | $8.3184 \times 10^{-4}$ | $1.3776 \times 10^{-3}$ | $1.9807 \times 10^{-3}$ | $2.6182 \times 10^{-3}$ | $3.2698 \times 10^{-3}$ | $3.9198 \times 10^{-3}$ | $4.5570 \times 10^{-3}$ |
| 0.1 | $4.3701 \times 10^{-4}$ | $9.9312 \times 10^{-4}$ | $1.6377 \times 10^{-3}$ | $2.3413 \times 10^{-3}$ | $3.0761 \times 10^{-3}$ | $3.8191 \times 10^{-3}$ | $4.5534 \times 10^{-3}$ | $5.2678 \times 10^{-3}$ |
| 0.2 | $1.2105 \times 10^{-3}$ | $2.6752 \times 10^{-3}$ | $4.2499 \times 10^{-3}$ | $5.8356 \times 10^{-3}$ | $7.3731 \times 10^{-3}$ | $8.8312 \times 10^{-3}$ | $1.0196 \times 10^{-2}$ | $1.1465 \times 10^{-2}$ |
| 0.3 | $1.7554 \times 10^{-3}$ | $3.7477 \times 10^{-3}$ | $5.7761 \times 10^{-3}$ | $7.7291 \times 10^{-3}$ | $9.5550 \times 10^{-3}$ | $1.1236 \times 10^{-2}$ | $1.2773 \times 10^{-2}$ | $1.4173 \times 10^{-2}$ |
| 0.4 | $1.8757 \times 10^{-3}$ | $3.8665 \times 10^{-3}$ | $5.8023 \times 10^{-3}$ | $7.6064 \times 10^{-3}$ | $9.2535 \times 10^{-3}$ | $1.0743 \times 10^{-2}$ | $1.2085 \times 10^{-2}$ | $1.3294 \times 10^{-2}$ |
| 0.5 | $1.6161 \times 10^{-3}$ | $3.2194 \times 10^{-3}$ | $4.7133 \times 10^{-3}$ | $6.0665 \times 10^{-3}$ | $7.2776 \times 10^{-3}$ | $8.3572 \times 10^{-3}$ | $9.3197 \times 10^{-3}$ | $1.0179 \times 10^{-2}$ |
| 0.6 | $1.1362 \times 10^{-3}$ | $2.1904 \times 10^{-3}$ | $3.1324 \times 10^{-3}$ | $3.9625 \times 10^{-3}$ | $4.6912 \times 10^{-3}$ | $5.3317 \times 10^{-3}$ | $5.8968 \times 10^{-3}$ | $6.3976 \times 10^{-3}$ |
| 0.7 | $6.2335 \times 10^{-4}$ | $1.1646 \times 10^{-3}$ | $1.6283 \times 10^{-3}$ | $2.0254 \times 10^{-3}$ | $2.3671 \times 10^{-3}$ | $2.6630 \times 10^{-3}$ | $2.9210 \times 10^{-3}$ | $3.1476 \times 10^{-3}$ |
| 0.8 | $2.3101 \times 10^{-4}$ | $4.1883 \times 10^{-4}$ | $5.7299 \times 10^{-4}$ | $7.0112 \times 10^{-4}$ | $8.0896 \times 10^{-4}$ | $9.0081 \times 10^{-4}$ | $9.7986 \times 10^{-4}$ | $1.0486 \times 10^{-3}$ |
| 0.9 | $3.5077 \times 10^{-5}$ | $6.1807 \times 10^{-5}$ | $8.2791 \times 10^{-5}$ | $9.9682 \times 10^{-5}$ | $1.1357 \times 10^{-4}$ | $1.2517 \times 10^{-4}$ | $1.3500 \times 10^{-4}$ | $1.4345 \times 10^{-4}$ |

| k \ n | 0.9 | 1.0 | 1.1 | 1.2 | 1.3 | 1.4 | 1.5 |
|---|---|---|---|---|---|---|---|
| 0.01 | $1.4696 \times 10^{-4}$ | $1.8048 \times 10^{-4}$ | $2.1654 \times 10^{-4}$ | $2.5459 \times 10^{-4}$ | $2.9413 \times 10^{-4}$ | $3.3471 \times 10^{-4}$ | $3.7594 \times 10^{-4}$ |
| 0.02 | $4.9001 \times 10^{-4}$ | $5.8264 \times 10^{-4}$ | $6.7834 \times 10^{-4}$ | $7.7582 \times 10^{-4}$ | $8.7401 \times 10^{-4}$ | $9.7206 \times 10^{-4}$ | $1.0693 \times 10^{-3}$ |
| 0.03 | $9.6713 \times 10^{-4}$ | $1.1288 \times 10^{-3}$ | $1.2921 \times 10^{-3}$ | $1.4552 \times 10^{-3}$ | $1.6166 \times 10^{-3}$ | $1.7754 \times 10^{-3}$ | $1.9308 \times 10^{-3}$ |
| 0.04 | $1.5427 \times 10^{-3}$ | $1.7777 \times 10^{-3}$ | $2.0114 \times 10^{-3}$ | $2.2416 \times 10^{-3}$ | $2.4670 \times 10^{-3}$ | $2.6863 \times 10^{-3}$ | $2.8989 \times 10^{-3}$ |
| 0.05 | $2.1914 \times 10^{-3}$ | $2.5009 \times 10^{-3}$ | $2.8052 \times 10^{-3}$ | $3.1020 \times 10^{-3}$ | $3.3899 \times 10^{-3}$ | $3.6680 \times 10^{-3}$ | $3.9358 \times 10^{-3}$ |
| 0.06 | $2.8934 \times 10^{-3}$ | $3.2771 \times 10^{-3}$ | $3.6507 \times 10^{-3}$ | $4.0123 \times 10^{-3}$ | $4.3605 \times 10^{-3}$ | $4.6948 \times 10^{-3}$ | $5.0149 \times 10^{-3}$ |
| 0.07 | $3.6331 \times 10^{-3}$ | $4.0891 \times 10^{-3}$ | $4.5299 \times 10^{-3}$ | $4.9536 \times 10^{-3}$ | $5.3594 \times 10^{-3}$ | $5.7470 \times 10^{-3}$ | $6.1165 \times 10^{-3}$ |
| 0.08 | $4.3971 \times 10^{-3}$ | $4.9230 \times 10^{-3}$ | $5.4282 \times 10^{-3}$ | $5.9111 \times 10^{-3}$ | $6.3714 \times 10^{-3}$ | $6.8091 \times 10^{-3}$ | $7.2249 \times 10^{-3}$ |
| 0.09 | $5.1743 \times 10^{-3}$ | $5.7673 \times 10^{-3}$ | $6.3336 \times 10^{-3}$ | $6.8725 \times 10^{-3}$ | $7.3840 \times 10^{-3}$ | $7.8687 \times 10^{-3}$ | $8.3276 \times 10^{-3}$ |
| 0.1 | $5.9553 \times 10^{-3}$ | $6.6119 \times 10^{-3}$ | $7.2362 \times 10^{-3}$ | $7.8276 \times 10^{-3}$ | $8.3869 \times 10^{-3}$ | $8.9153 \times 10^{-3}$ | $9.4141 \times 10^{-3}$ |
| 0.2 | $1.2641 \times 10^{-2}$ | $1.3727 \times 10^{-2}$ | $1.4732 \times 10^{-2}$ | $1.5661 \times 10^{-2}$ | $1.6521 \times 10^{-2}$ | $1.7319 \times 10^{-2}$ | $1.8060 \times 10^{-2}$ |
| 0.3 | $1.5448 \times 10^{-2}$ | $1.6610 \times 10^{-2}$ | $1.7671 \times 10^{-2}$ | $1.8642 \times 10^{-2}$ | $1.9533 \times 10^{-2}$ | $2.0353 \times 10^{-2}$ | $2.1109 \times 10^{-2}$ |
| 0.4 | $1.4385 \times 10^{-2}$ | $1.5372 \times 10^{-2}$ | $1.6268 \times 10^{-2}$ | $1.7082 \times 10^{-2}$ | $1.7826 \times 10^{-2}$ | $1.8508 \times 10^{-2}$ | $1.9134 \times 10^{-2}$ |
| 0.5 | $1.0950 \times 10^{-2}$ | $1.1643 \times 10^{-2}$ | $1.2270 \times 10^{-2}$ | $1.2837 \times 10^{-2}$ | $1.3354 \times 10^{-2}$ | $1.3826 \times 10^{-2}$ | $1.4258 \times 10^{-2}$ |
| 0.6 | $6.8436 \times 10^{-3}$ | $7.2427 \times 10^{-3}$ | $7.6017 \times 10^{-3}$ | $7.9260 \times 10^{-3}$ | $8.2203 \times 10^{-3}$ | $8.4884 \times 10^{-3}$ | $8.7336 \times 10^{-3}$ |
| 0.7 | $3.3480 \times 10^{-3}$ | $3.5263 \times 10^{-3}$ | $3.6859 \times 10^{-3}$ | $3.8294 \times 10^{-3}$ | $3.9592 \times 10^{-3}$ | $4.0771 \times 10^{-3}$ | $4.1847 \times 10^{-3}$ |
| 0.8 | $1.1088 \times 10^{-3}$ | $1.1620 \times 10^{-3}$ | $1.2094 \times 10^{-3}$ | $1.2517 \times 10^{-3}$ | $1.2899 \times 10^{-3}$ | $1.3244 \times 10^{-3}$ | $1.3558 \times 10^{-3}$ |
| 0.9 | $1.5078 \times 10^{-4}$ | $1.5720 \times 10^{-4}$ | $1.6286 \times 10^{-4}$ | $1.6791 \times 10^{-4}$ | $1.7242 \times 10^{-4}$ | $1.7648 \times 10^{-4}$ | $1.8016 \times 10^{-4}$ |

5. The shear stress can be calculated as:

$$\tau = \gamma\eta$$

Figure 7:
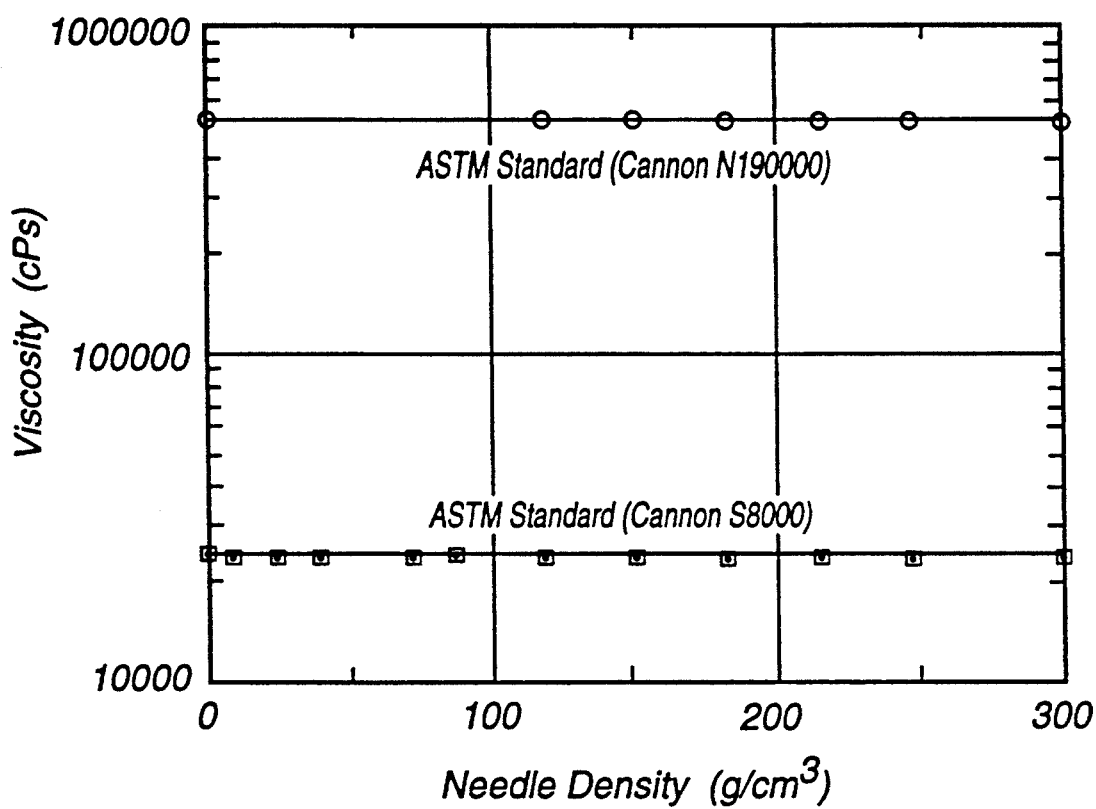
FIG. 7 is a plot of viscosity measured by using the present controlled needle viscometer compared to the viscosity data known of ASTM Standards (Cannon S-8000 and N190000).
Figure 8:
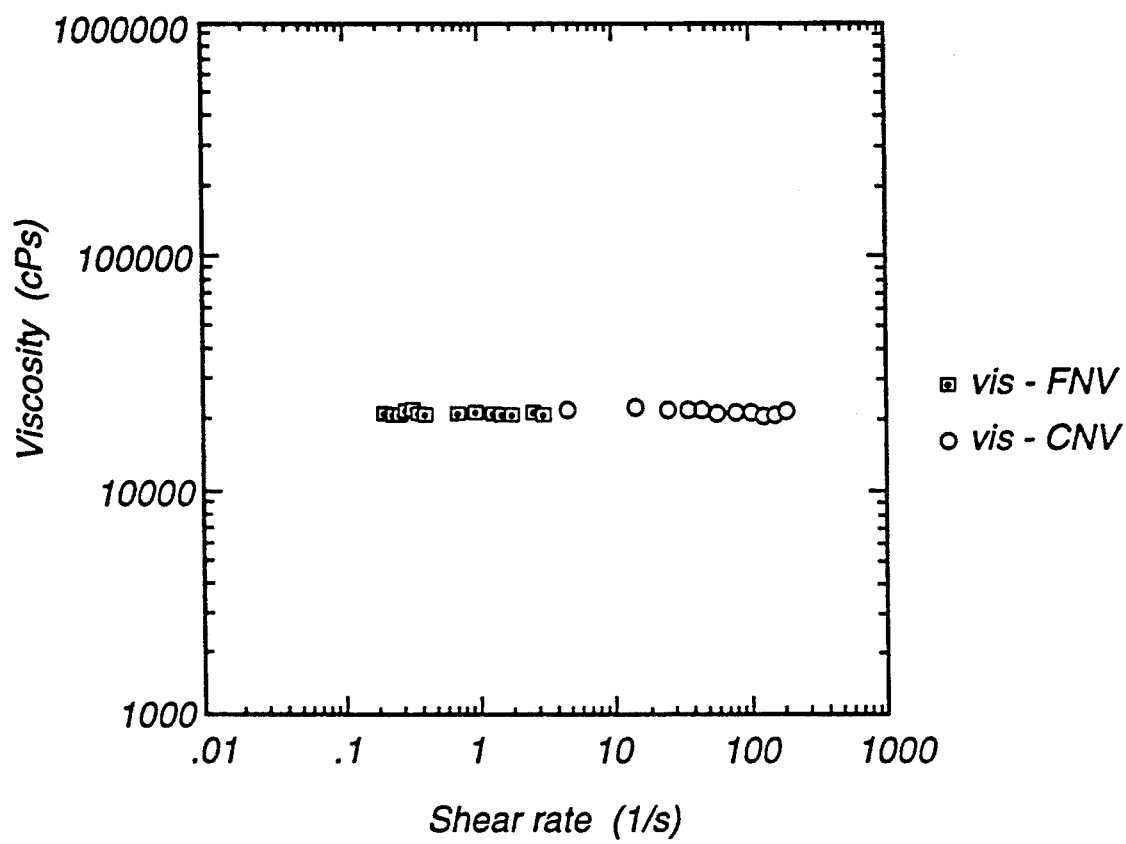
FIG. 8 is a plot of viscosity measured by using the present controlled needle viscometer compared to the data measured by a prior art falling needle viscometer, for printing ink raw material.

The values for $A(k_2,n)$ and $B(k_2,n)$ have been calculated for varying $k_2$ and $n$ values for the modified power law model for non-Newtonian fluids and can be obtained from Tables 1 and 2 above. As shown in FIG. 7, the viscosity data of ASTM standard Cannon S-8000 and N190000 are compared to the viscosity measured by using the controlled needle viscometer. The difference between ASTM standard viscosity and the data measured by the controlled needle viscometer is within 1.28%, which is an excellent agreement considering experimental errors. As shown in FIG. 8, the printing ink raw material viscosity measured by the falling needle ("FNV") and controlled needle viscometer ("CNV") is plotted. Again, the viscosity data measured by two viscometers agreed well.

It can be observed that the controlled needle viscometer of the present invention is suitable for measuring the viscosity of thin and thick material at low and high shear rates.

From the foregoing, the advantages of the present apparatus and method over prior art falling needle viscometers should now be apparent:

1. The apparatus is simple to construct; only one controlled needle is needed for the viscosity measurement.
2. The density of the controlled needle 1 can be adjusted by adding the weights 7 at the tip of the bar 16 connected to the controlled needle, so that a velocity of fall of almost 0 cm per second to about 50 cm per second can be obtained without changing needles.
3. The controlled needle 1 falls vertically since the controlled needle is guided by the controlled needle guide 8 and the weights 7 or electric or magnetic forces at the top of the controlled needle 1 are concentric with the bar 16.
4. It is easy to change the shear rates since only one controlled needle 1, with different weights 7, is dropped and lifted manually or by an automatic mechanism (not illustrated). This is not like the prior art falling needles, of which several different density needles are required to change the shear rates.
5. Cleaning of a controlled needle is easy, because a user can remove a controlled needle from the sample insert tube without contacting the fluid. Also the sample insert tube can be disposable.
6. It is easy to measure extremely highly viscous materials such as gels and pastes, since the density of a controlled needle can be adjusted to greater than 2000 g/cm³, whereas the maximum density of falling needle is only about 8 g/cm³.
7. It is easy to measure the extremely high shear rate for low viscosity liquids, like engine oils and lubricants.
8. The viscosity of extremely high temperature, greater than 1500° C., liquids, such as melted plastics and metals, can be measured, using light sensor or laser means.
9. Viscosity of paramagnetic liquids also can be measured with light sensor or laser means.
10. continuous shear rate, viscosity and shear stress can be measured with the gradual fall of a controlled needle by using pushing force produced by changing electronic motor speed and laser or light sensor to measure falling time.

The apparatus is simple and easy to use, and equations for the accurate determination of viscosity for Newtonian and non-Newtonian fluids from the data collected by the apparatus have been derived.

The present invention may be embodied in other specific forms without departing from its spirit or essential attributes. Accordingly, reference should be made to the appended claims, rather than the foregoing specifications as indicating the scope of the invention.

I claim:

1. An apparatus for determining the viscosity of fluids, comprising:
    a vertically oriented sample insert tube for holding fluid whose viscosity is to be determined, said sample insert tube having a cylindrical wall having an internal diameter and a vertical axis;
    means operatively associated with said sample insert tube for maintaining said sample insert tube at a constant temperature;
    a controlled needle received in said sample insert tube for axial movement therein, said controlled needle comprising an elongated cylindrical body having an external diameter and rounded ends and having an upwardly extending guide rod coupled to one of said ends in axial alignment with said body, a weight support associated with said rod, whereby weight may selectively be applied to said controlled needle, said body having a length of at least twice the internal diameter of said sample insert tube and the diameter of said body being equal to or less than 0.95 times the internal diameter of said sample insert tube;
    a guide surface operatively associated with said sample insert tube at an upper end thereof and adapted to receive and engage said guide rod, whereby said guide surface and said guide rod maintain said controlled needle coaxial with the vertical axis of said sample insert tube;
    markings on said cylindrical wall of said sample insert tube, said markings being spaced by a predetermined distance indicative of distance of fall of said controlled needle within said sample insert tube;
    and means operatively associated with said markings for measuring the time of fall of the controlled needle through the predetermined distance.

2. Apparatus in accordance with claim 1, wherein the diameter of said body is 0.1 to 4.0 cm and the length of the body is 1 cm to 20 cm.

3. Apparatus in accordance with claim 2, wherein the diameter of said body is 1 cm and the length of the body is 5 cm.

4. For use in a cylindrical sample insert tube of inside diameter D, a controlled needle for measuring the viscosity of Newtonian and non-Newtonian fluids in the sample insert tube, comprising: an elongated cylindrical body member having an outer diameter and rigid side walls and a sealed generally hemispherical end portion, means associated with said body member to facilitate adjustment of the density of the needle to adjust the velocity of fall of the needle through the fluid whose viscosity is to be measured, said means associated with said member comprising a rod coupled to one end of said body member in axial alignment with said body member, said rod having means thereon for receiving and supporting weights externally of said body member, and said body having a length of at least 2D and a diameter such that the ratio of the diameter of the body member to the diameter of the sample insert tube is between 0.2 to 0.95, the diameter of said body member being 0.1 to 4.0 cm and its length being 1 to 20 cm.

5. A method for determining the viscosity of a Newtonian fluid, comprising the steps of:
    a. providing a sample insert tube having a diameter D;

b. filling the sample insert tube with a fluid for which the viscosity is to be determined;

c. providing a controlled needle having a diameter $d_2$ and a length N, and having attached thereto a rod extending out of said sample insert tube and having a diameter $d_1$, such that the ratio $k_2=d_2/D$ is at most 0.95 and N/D is at least 2.0, said step of providing a controlled needle including the further step of adjusting the density of the controlled needle by applying to the needle weights external of the needle to control the velocity of the needle through the fluid;

d. inserting the controlled needle into the fluid filled sample insert tube;

e. maintaining a constant temperature in the fluid filled sample insert tube;

f. allowing the temperature of the controlled needle to reach the temperature of the fluid;

g. allowing the controlled needle to fall through the fluid filled sample insert tube;

h. measuring the time, t seconds, taken for the controlled needle to fall a predetermined distance F relative to the wall of the sample insert tube; and i. calculating the viscosity.

6. A method in accordance with claim 5, wherein the weights applied to the controlled needle are sufficient to produce a velocity of the needle through the fluid of up to 50 cm per second.

7. A method in accordance with claim 5, wherein said step of calculating the viscosity (7) is performed by means of the following equations:

$$\eta = \frac{(\rho_s - \rho_f)g}{UG} = \frac{(\rho_s - \rho_f)g}{(U_t/ECF)G}$$

where $$G = \frac{8(1 + k_2^2)}{k_2^2(1 - \ln k_2) - (1 + \ln k_2)} \cdot \frac{1}{d_2^2}$$

$$ECF = \frac{1 + (2/3)(d_2/L_2) + (d_1/d_2)^2(L_1/L_2)}{1 + (3/(2C_w))(d_2/L_2)(1/B_2) + (L_1/L_2)(B_1/B_2)}$$

$$B_1 = \frac{k_1^2 + 1}{(k_1^2 - 1) - (k_1^2 + 1)\ln k_1}$$

$$B_2 = \frac{k_2^2 + 1}{(k_2^2 - 1) - (k_2^2 + 1)\ln k_2}$$

$C_w = 0.9999456 - 2.08324 k_2 - 0.2822582 k_2^2 + 3.392001 k_2^3 - 2.58148 k_2^4 + 0.554073 k_2^5$ $k_1 = d_1/D$
$k_2 = d_2/D$
$C_w$ = the wall correction factor of sphere
$d_1$ = diameter of the bar
$d_2$ = diameter of the controlled needle 1 or diameter of hemispherical tips of needle
D = the inside diameter of sample insert tube
ECF = End Correction Factor of the controlled needle
F = Predetermined distance of fall
$L_1$ = (immersed length of bar 16 before controlled needle is allowed to fall) plus (a half of predetermined distance of fall)
$L_2$ = controlled needle length minus one diameter of controlled needle
$\rho_s$ = density of controlled needle
$\rho_f$ = density of fluid g = gravity constant
t = the time of fall
$U_t$ = terminal velocity of controlled needle (F/t)
$U = U_t/ECF$.

8. A method for determining the viscosity of a non-Newtonian fluid, comprising the steps of:

a. providing a sample insert tube having a diameter D;

b. filling the sample insert tube with a fluid for which the viscosity is to be determined;

c. providing a controlled needle having a diameter $d_2$ and a length N, and having attached thereto a bar having a diameter $d_1$, such that $k_2=d_2/D$ is at most 0.95 and N/D is at least 2.0, said step of providing a controlled needle including the further step of adjusting the density of the controlled needle by applying to the needle weights external to the needle to produce a velocity of the needle through the fluid of almost 0 to 50 cm per second.

d. inserting the controlled needle into the fluid filled sample insert tube;

e. maintaining a constant temperature in the fluid filled sample insert tube;

f. allowing the temperature of the controlled needle to reach the temperature of the fluid;

g. allowing the controlled needle to fall through the fluid filled sample insert tube;

h. measuring the time, t seconds, taken for the controlled needle to fall between predetermined distance F relative to the wall of the sample insert tube; and i. calculating the viscosity.

9. A method in accordance with claim 8, wherein the weights applied to the controlled needle are sufficient to produce a velocity of the needle through the fluid of 50 cm per second.

10. A method in accordance with claim 8, wherein said step of calculating the viscosity (9) is performed by means of the following equations:

i) U is calculated as follows:

$$U = U_t/ECF = (F/t)(1/ECF)$$

where $$ECF = \left[ \frac{1 + (2/3)(d_2/L_2) + (d_1/d_2)^2(L_1/L_2)}{1 + (3/2C_w)(d_2/L_2)(1/B_2) + (L_1/L_2)(B_1/B_2)} \right]^{1/n}$$

$$B_1 = \frac{k_1^2 + 1}{(k_1^2 - 1) - (k_1^2 + 1)\ln k_1}$$

$$B_2 = \frac{k_2^2 + 1}{(k_2^2 - 1) - (k_2^2 + 1)\ln k_2}$$

$C_w = 0.9999456 - 2.08324 k_2 - 0.2822582 k_2^2 + 3.392001 k_2^3 - 2.58148 k_2^4 + 0.554073 k_2^5$ $k_1 = d_1/D$
$k_2 = d_2/D$
$C_w$ = the wall correction factor of sphere
$d_1$ = diameter of the bar
$d_2$ = diameter of the controlled needle or diameter of hemispherical tips
D = the inside diameter of sample insert tube
ECF = End Correction Factor of the controlled needle
F = predetermined distance of fall $L_1$ = (immersed bar length before dropping controlled needle) plus (a half of predetermined distance of fall $L_2$ = controlled needle length minus one diameter of controlled needle $\rho_s$ = density of controlled needle $\rho_f$ = density of fluid g = gravity constant t = the time of fall $U_t$ = terminal velocity of controlled needle (F/t)

(ii) the flow index, n, where:

$$n = \frac{d[\ln(\rho_s - \rho_f)]}{d[\ln U]}$$

is determined from the slope of ln $(\rho_s - \rho_f)$ vs. ln U (iii) Whereby the shear rate can then be calculated as follows:

$$\gamma = 2UA(k_2,n)/D$$

where $A(k_2,n)$ = dimensionless number; and (iv) The viscosity is then calculated as follows:

$$\eta = \frac{(\rho_s - \rho_f)gD^2 B(k_2, n)}{4U}$$

where $B(k_2,n)$, a dimensionless number.

* * * * *